(12) United States Patent
Buydts et al.

(10) Patent No.: US 9,980,905 B2
(45) Date of Patent: May 29, 2018

(54) DOSAGE FORM ARTICLES

(71) Applicant: Capsugel Belgium NV, Bornem (BE)

(72) Inventors: Hilde Buydts, Antwerp (BE); Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days. days.

(21) Appl. No.: 15/032,601

(22) PCT Filed: Dec. 3, 2014

(86) PCT No.: PCT/IB2014/066565
§ 371 (c)(1),
(2) Date: Apr. 27, 2016

(87) PCT Pub. No.: WO2015/083105
PCT Pub. Date: Jun. 11, 2015

(65) Prior Publication Data
US 2016/0256384 A1    Sep. 8, 2016

Related U.S. Application Data

(60) Provisional application No. 61/911,070, filed on Dec. 3, 2013.

(51) Int. Cl.
*A61K 9/00* (2006.01)
*A61K 9/48* (2006.01)
(Continued)

(52) U.S. Cl.
CPC .............. *A61K 9/0097* (2013.01); *A61J 7/04* (2013.01); *A61K 9/0009* (2013.01);
(Continued)

(58) Field of Classification Search
CPC ....... A61J 7/04; A61K 9/0009; A61K 9/0053; A61K 9/0097; A61K 9/4808; G06F 19/3462; G08B 21/24
(Continued)

(56) References Cited

U.S. PATENT DOCUMENTS 4,893,721 A * 1/1990 Bodenmann ............ A61J 3/072
206/530
4,972,969 A * 11/1990 Randklev ................ A61C 5/62
206/219

(Continued)

FOREIGN PATENT DOCUMENTS

CA    2932562    6/2015
EP    1301178    1/2007
(Continued)

OTHER PUBLICATIONS

International Preliminary Report on Patentability for PCT/IB2014/066565 (dated Jun. 16, 2016).
(Continued)

*Primary Examiner* — Nader Bolourchi
(74) *Attorney, Agent, or Firm* — Klarquist Sparkman, LLP

(57) ABSTRACT

A dosage form article suitable for oral administration may include more than one compartment, each formed by a plurality of distinct segments of the dosage form article. The dosage form article may also include a signaling means and a drug, wherein the signaling means and the drug are each stored in different compartments physically separated from one another. Both the drug and the signaling means may be wholly incorporated within the dosage form article, the respective compartments being arranged to fully enclose the drug and signaling means only when at least two of the plurality of distinct segments are connected.

17 Claims, 5 Drawing Sheets

(51) Int. Cl.
*A61J 7/04* (2006.01)
*G06F 19/00* (2018.01)
*G08B 21/24* (2006.01)

(52) U.S. Cl.
CPC .......... *A61K 9/0053* (2013.01); *A61K 9/4808* (2013.01); *G06F 19/3462* (2013.01); *G08B 21/24* (2013.01)

(58) Field of Classification Search
USPC ...................................................... 340/573.1
See application file for complete search history.

(56) References Cited

U.S. PATENT DOCUMENTS

| | | | | |
|---|---|---|---|---|
| 5,750,143 | A * | 5/1998 | Rashid | A61K 9/4808 424/451 |
| 5,769,267 | A * | 6/1998 | Duynslager | A61J 3/071 220/4.21 |
| 8,547,248 | B2 * | 10/2013 | Zdeblick | A61B 5/0028 340/870.28 |
| 9,561,189 | B2 | 2/2017 | Buydts et al. | |
| 2003/0150832 | A1 * | 8/2003 | Bakhshaee | A61K 9/4808 215/10 |
| 2005/0008690 | A1 | 1/2005 | Miller | |
| 2006/0289640 | A1 * | 12/2006 | Mercure | A01K 11/007 235/435 |
| 2007/0237719 | A1 * | 10/2007 | Jones | A61B 5/06 424/9.2 |
| 2008/0175898 | A1 * | 7/2008 | Jones | A61B 5/0002 424/452 |
| 2013/0081358 | A1 | 4/2013 | Boldis et al. | |

FOREIGN PATENT DOCUMENTS

| | | |
|---|---|---|
| EP | 2049064 | 10/2010 |
| EP | 2211820 | 5/2012 |
| EP | 2076954 | 10/2016 |
| EP | 3077086 | 10/2016 |
| JP | 2017500104 | 1/2017 |
| WO | WO2006/127355 | 11/2006 |
| WO | WO2007/017725 | 2/2007 |
| WO | WO2008/089232 | 7/2008 |
| WO | WO2008/112578 | 9/2008 |
| WO | WO2009/138920 | 11/2009 |
| WO | WO2010/107980 | 9/2010 |
| WO | WO2015/083105 | 6/2015 |

OTHER PUBLICATIONS

European Search Report and Opinion issued for European Patent Application No. EP13195563.5 (dated Apr. 29, 2014).
International Search Report and Written Opinion for PCT/IB2014/002650 (dated Apr. 16, 2015).
International Search Report and Written Opinion for PCT/IB2014/066565 (dated May 8, 2015).

* cited by examiner

DOSAGE FORM ARTICLES

CROSS REFERENCE TO RELATED APPLICATIONS

This is the U.S. National Stage of International Application No. PCT/IB2014/066565, filed Dec. 3, 2014, which was published in English under PCT Article 21(2), which in turn claims the benefit of U.S. Provisional Application No. 61/911,070, filed Dec. 3, 2013, both of which are incorporated herein in their entities.

FIELD

The present disclosure relates to ingestible dosage form articles, preferably multi-part capsules, for the delivery of a drug and an ingestible signaling means to deliver both a predefined signal and a medicinal effect. More particularly, the dosage form articles are suitable for ingestion by a subject, preferably the subject being selected from humans or animals. The ingestible dosage form articles being arranged to effectively provide a signal without the signaling means compromising drug stability and effectiveness or the drug compromising on signal quality and strength.

Dosage form articles disclosed herein may be used as part of diagnostic and therapeutic activities, in particular for recording adherence to a medicinal regimen.

Dosage form articles herein may also be used to enable the subject to determine the state of the drug by processing a signal received directly from the dosage form article. For example, dosage form articles herein may provide one or more signals to a subject regarding the state of the drug within the dosage form article and enable the subject to, for example, identify whether still safe to ingest the dosage form article containing the drug by simply receiving and processing the signal provided by the signaling means stored within the dosage form article.

BACKGROUND

Prescription medications are effective remedies for many patients when taken according to the respective medical regimen proposed by medical practitioners as well as when taken prior to exposure to high temperatures and/or before expiry of the drug. If not followed, the latter may lead to significant undesirable effects on the subject.

It may be desirable to monitor strict adherence to a given medical regimen in order to, for example, enable effective clinical studies, reduce negative impact on patients, and reduce negative impacts on the healthcare system in general (e.g. hospitalization numbers, admission to nursing homes etc.).

It may further be desirable to simplify the task of the subject when taking such medications. For example, it is desirable that the dosage form itself be capable of communicating to the subject whether it is safe to ingest a given drug (e.g. whether it has been exposed to high temperatures, high enough to degrade one or more compounds in the drug, or whether the expiry date of the drug has been reached/passed, etc.). The latter ensures that a subject not having access to the box of the medicament (e.g. miss-placed) or having sight problems not allowing to read the print on the box to still know whether safe or not to ingest directly by information provided by the dosage form article itself.

It may be further desirable to assist a subject in knowing when a certain medication should be taken. The latter is particularly true for subjects who need to take several combination of medications and all at different intervals.

It may also be desirable to assist a subject in knowing whether a certain medicament is running out and provide an alert to the subject that a new prescription should be requested to continue the cure without the risk of interruption.

Some attempts have been made to address some or part of the above desires, some technologies appearing more successful than others.

For example, in-body devices having deployable antennas have been developed to provide a signal upon contact with a target physiological site, such as described in WO2008/112578. However, such devices have problems of subject acceptance (when antennas are adhered to the outer surface of the dosage form) as well as impacting swallowing of the device and further may lead to drug/signal incompatibilities, added to this is that such devices still do not enable identification of the drug status nor enable addressing some of the other above identified desires.

Other devices, such as those described in WO2010/107980, provide alternative passive signaling means on the outer surface of medication capsules. Again, this leads to subject acceptance issues, swallowability, as well as premature release and activation of the signaling means.

Other devices, such as those described in US2008/0175898A1 provide for signaling means positioned on or integrally with an upper capsule portion, and a drug stored within a lower capsule portion. This configuration has the disadvantage of limiting flexibility in signaling means placement and filling as well as manufacturing complexity (when the latter is positioned integrally with the upper capsule portion) and subject acceptance issues, swallowability, as well as premature release and activation of the signaling means (when the latter is positioned on the capsule). Moreover, a portion of the signaling means may be exposed to a compartment storing the drug or a volume external to the dosage form. The latter may result in drug contamination as well as signal interference depending on the drug and physical state of the drug (particularly when the signaling means is exposed to the drug) as well as premature triggering of the signaling means, increased risk of damage during handling, and swallowing issues (particularly when a portion of the signaling means is exposed to the volume external to the dosage form).

Therefore there still remains a need to overcome the problems of the prior art and achieve the above identified desires via novel dosage form articles and methods.

BRIEF SUMMARY

A first aspect of the present disclosure relates to a dosage form article suitable for oral administration, comprising more than one compartments each formed by a plurality of distinct segments of the dosage form article, the dosage form article comprising a signaling means and a drug, wherein the signaling means and the drug are each stored in different compartments physically separated from one another, and wherein both the drug and the signaling means are wholly incorporated within the dosage form article, the respective compartments being arranged to fully enclose the drug and signaling means only when at least two of the plurality of distinct segments are connected.

A further aspect of the present disclosure relates to a method of measuring compliance with a medical regimen may comprise the steps of: administering to a subject a dosage form article; providing a receiver for detecting a signal produced by the signaling means preferably when the dosage form reaches a predetermined position in the gastrointestinal tract of the subject; and optionally recording administration parameters via a recording device which may be in electrical communication with said receiver, said administration parameters preferably selected from the group consisting of date, time, and combinations thereof.

A further aspect of the present disclosure relates to a method for determining whether it is safe to ingest a medicament may comprise the steps of: providing a dosage form article; comparing a signal received by the signaling means to a predetermined scale to instruct a subject whether he should or should not ingest said dosage form. The predetermined scale may be in the form of a written scale provided with the medicament and/or stored on a website and/or cloud computing, the latter such that it may be accessed by the subject or user via the use of any personal computer or even directly by a processing device that the subject may use to capture the signal from the signaling means.

A further aspect of the present disclosure relates to a method for the automatic prompting of a subject to take a medicament, the method comprising the steps of: providing a portable communication device arranged to provide a warning, preferably selected from visual, sound, and combinations thereof, to a subject when it is time to ingest a medicament; providing a dosage form article; providing a receiver capable of detecting a signal generated by the signaling means, the receiver being arranged to provide a further signal to a processing device, the processing device capable of recording said further signal and to instruct the communication device to stop providing said warning; and allowing said receiver to detect said signaling means; wherein said warning is de-activated only when the subject places said receiver proximal to said dosage form, and the signaling means stored therein is detected.

A further aspect of the present disclosure relates to a method of assembly, of dosage form articles, comprising the steps of: providing a first body part; inserting a signaling means within the first body part; providing a second body part; filling said second body part with a drug; optionally closing said second body part by locking a second cap part thereon; inserting said second body part within said first body part such that the signaling means is further located into a firm position between said first and second body parts; and closing said first body part by locking a first cap part thereon. In a preferred embodiment the method of assembly comprises the sequential steps of: providing a first body part; inserting a signaling means within the first body part; providing a second body part; inserting said second body part within said first body part such that the signaling means is further located into a firm position between said first and second body parts and typically such that a volume in the first body part is closed off by the second body part to form a signaling means compartment; optionally locking said second body part to said first body part typically via a snap fit; filling said second body part with a drug; and closing said second body part by locking a first cap part onto said second body part, first body part or both, typically via a snap fit.

DETAILED DESCRIPTION

Figure 1:
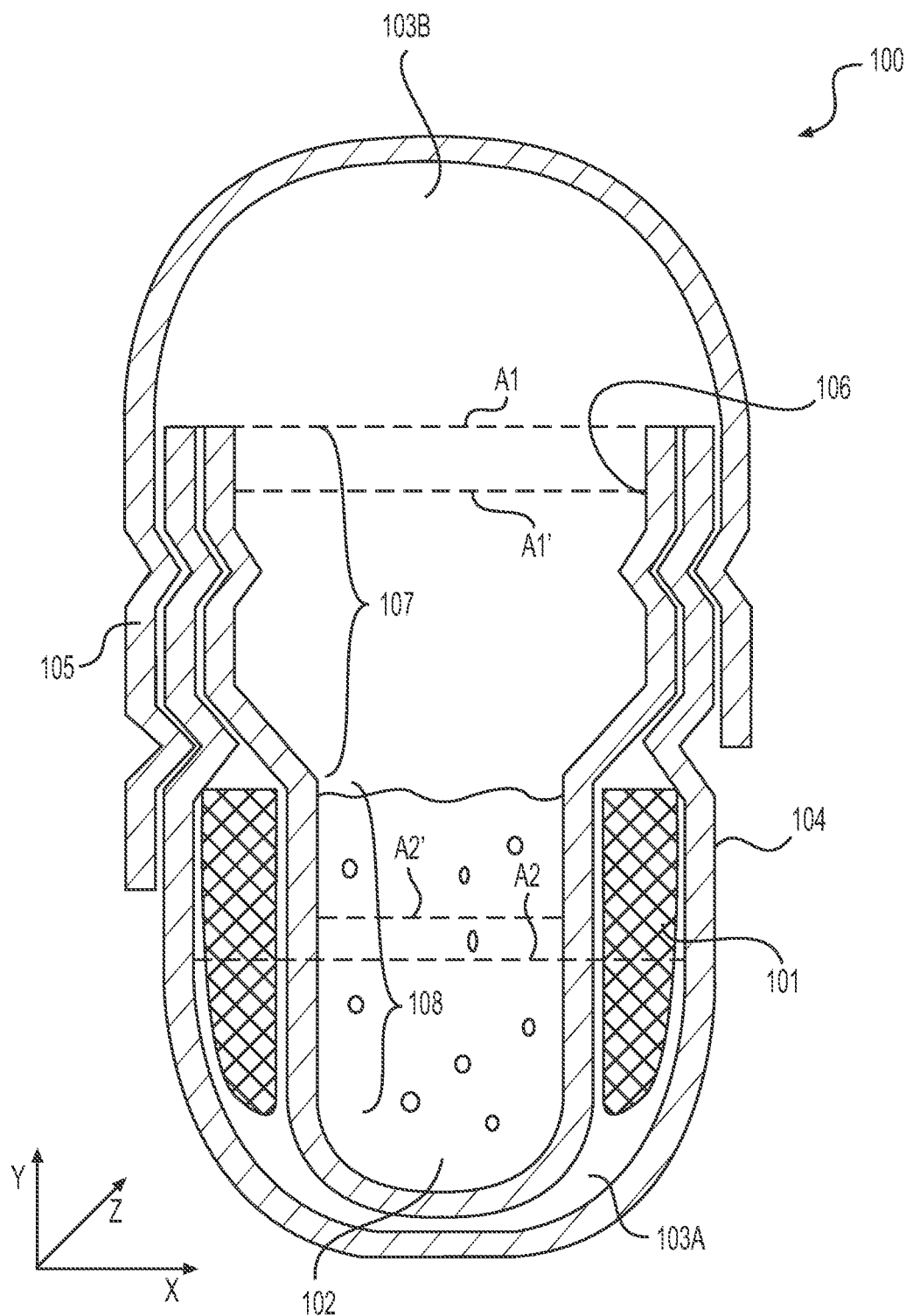
FIG. 1 is an illustration of a cross-sectional view of a dosage form article according to one aspect of the disclosure.

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which returns to its un-deformed shape upon the removal of a deforming force. Typically such shells may comprise, for example, less than 25%, preferably less than 20%, more preferably from 0% to 14%, even more preferably from greater than 0% to less than 14%, water by weight.

By the term "wholly incorporated", it is intended that the element referred to is fully contained within the dosage form article such that no surfaces of said element are directly in contact with any portion of a volume external to the dosage form article. Such generally being formed when the dosage form article is in assembled state.

By the term "compartment", it is intended as a definite volume for storing a drug, or signaling means therein, each volume being formed and delimited by multiple parts (i.e. a plurality of distinct segments) when connected to each other.

By the term "multiple parts" or "plurality of distinct segments", it is intended the portions making up the dosage form article which, when connected, form one or more compartments. Such portions are separate components and typically comprise (or consist of) cap part(s), body part(s) and combinations thereof.

By the term "arranged within" it is intended that, for example, at least 70%, preferably at least 80%, more preferably at least 90%, even more preferably more than 95%, most preferably 100%, of the surface area of the element referred to is located inside the other element referred to.

Various embodiments will now be described to provide an overall understanding of the principles of the structure, function, manufacture, and use of dosage form articles and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

Dosage Form Articles

Referring to FIGS. 1 to 5, the disclosure herein relates to a dosage form article 100, 200, 300, 400, 500 suitable for oral administration, comprising more than one compartments 103a, 103b, 203a, 203b, 303a, 303b, 403a, 403b each formed by a plurality of distinct segments 104, 105, 106, 204, 205, 206, 207, 304, 305, 306, 404, 405, 406 of the dosage form article 100, 200, 300, 400, said dosage form article comprising a signaling means 101, 201, 301, 401 and a drug 102, 202, 302, 402, wherein said signaling means 101, 201, 301, 401 and said drug 102, 202, 302, 402 are each stored in different compartments 103a, 103b, 203a, 203b, 303a, 303b, 403a, 403b physically separated from one another, and wherein both said drug 102, 202, 302, 402 and said signaling means 101, 201, 301, 401 are wholly incorporated within said dosage form article 100, 200, 300, 400, the respective compartments being arranged to fully enclose said drug 102, 202, 302, 402 and signaling means 101, 201, 301, 401 only when at least two of said plurality of distinct segments 104, 105, 106, 204, 205, 206, 207, 304, 305, 306, 404, 405, 406 are connected. Advantages of this arrangement are that contamination of the drug by the signaling means or disturbance of the signaling means by the drug is avoided. Moreover, the signaling means still remains protected within the dosage form article, thus permitting better control over the release of the signal by the signaling means as well as ensuring swallowability of the dosage form article is not compromised. Further advantages are to the flexibility of signaling means location as well as reduced manufacturing or filling complexity, and material saving. Preferably the dosage form is a hard shell capsule.

The dosage form article 100, 200, 300, 400, 500 may comprise a translucent portion of the dosage form article 100, 200, 300, 400, 500 such that the signaling means 101, 201, 301, 401 is visible through said dosage form 100, 200, 300, 400, 500. This is particularly advantageous when the signaling means is in the form of indicia providing a signal via for example a change of color or barcode-like medium, thus enabling a subject or scanner/receiver to receive said signal and process it accordingly. The latter whilst still ensuring that the signaling means remains protected from the outside environment.

The inner compartment may be transparent or opaque, preferably opaque. The latter is particularly advantageous when the signaling means is in the form of indicia as this improves the contrast desirable for reading the signal.

The compartment 103a, 203a, 303a, 403a storing the signaling means 101, 201, 301,401 and the compartment 103b, 203b, 303b, 403b storing the drug 102, 202, 302, 402 may have different dissolution properties, preferably the compartment 103a, 203a, 303a, 403a storing said signaling means 101, 201, 301,401 may be arranged to disintegrate faster than the compartment 103b, 203b, 303b, 403b storing the drug 102, 202, 302, 402. This has the advantage that the drug is released at a different time versus the signaling means. It has the further advantage that a signal may be provided starting from shortly after ingestion to just prior the drug being released.

The compartment storing the signaling means may comprise one or more openings, said openings may be from 500 μm to 2000 μm, preferably from 800 μm to 1500 μm, in diameter. This has the advantage to allow fluids to enter the compartment storing the signaling means such that the latter may be activated (e.g. upon reaching a predetermined pH in reaction to in-body acids) or to allow certain pre-subministration parameters to be recorded (e.g. humidity).

Figure 2:
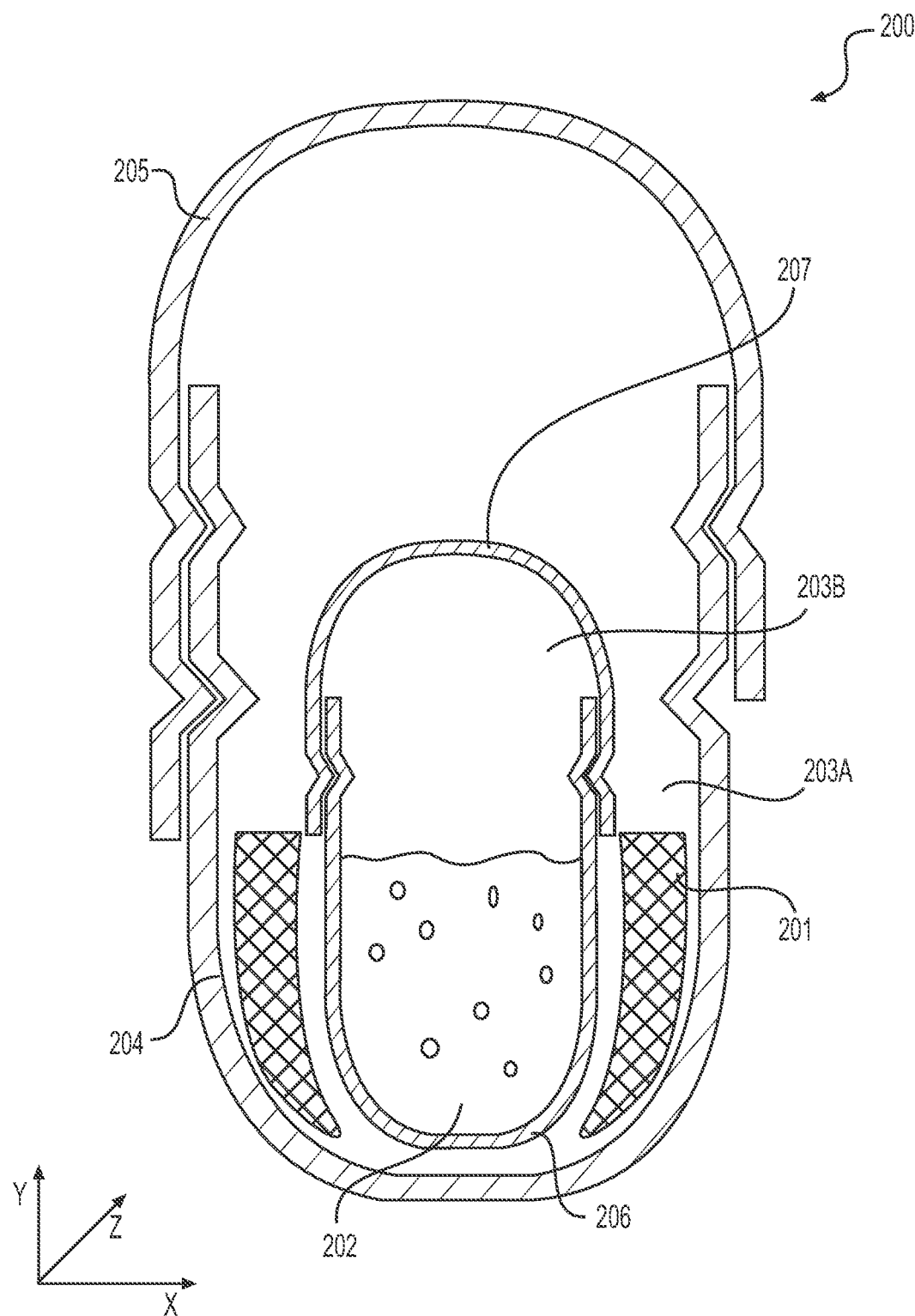
FIG. 2 is an illustration of a cross-sectional view of a dosage form article according to one aspect of the disclosure.

Referring to FIG. 2, the dosage form article 200 may comprise: at least one first body part 204 and at least one first cap part 205, wherein said first body and cap parts 204, 205 are telescopically engageable to provide a first compartment 203a; and at least one second body part 206 and at least one second cap part 207, wherein said second body and cap parts 206, 207 are telescopically engageable to provide a second compartment 203b; wherein said second compartment 203b is stored within said first compartment 203a, the signaling means 201 being stored within the first or second compartment 203a, 203b and the drug 202 being stored within the first or second compartment 203a, 203b, and wherein said signaling means 201 and said drug 202 are stored in different compartments.

It is understood that dosage forms described herein may comprise a plurality of said second compartments, stored within one another and each may have different dissolution properties. This has the advantage that multiple different drugs and/or multiple different signaling means may be stored within a single dosage form article, and may be released at different predetermined positions in the gastrointestinal tract.

The signaling means 201 may be stored within the first compartment 203a and the drug 202 may be stored within the second compartment 203b, preferably wherein the first body and/or cap parts 204, 205 may be translucent such that the signaling means 201 may be seen through the first compartment 203a. The second body and/or cap parts may be opaque.

Figure 3:
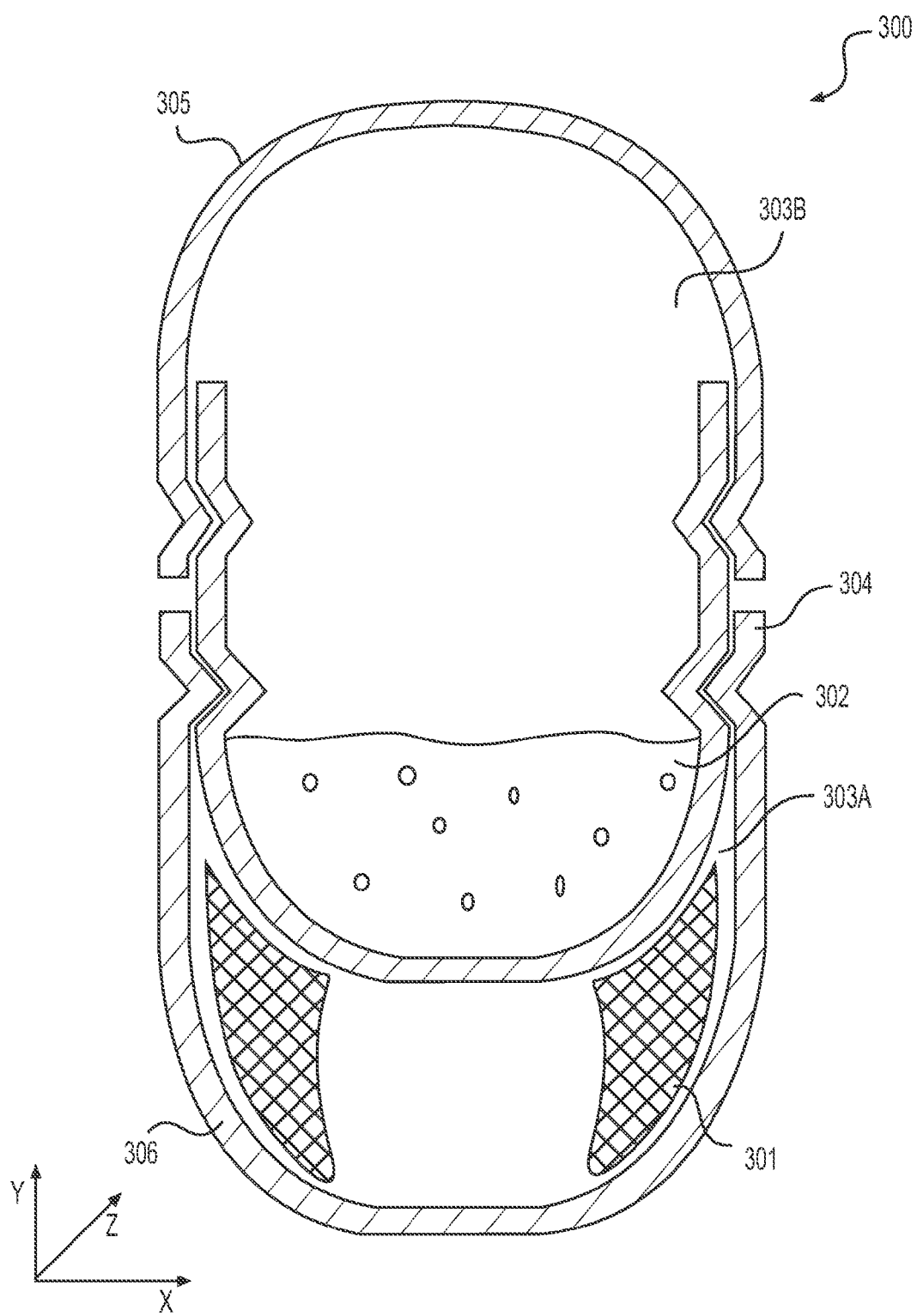
FIG. 3 is an illustration of a cross-sectional view of a dosage form article according to one aspect of the disclosure.
Figure 4:
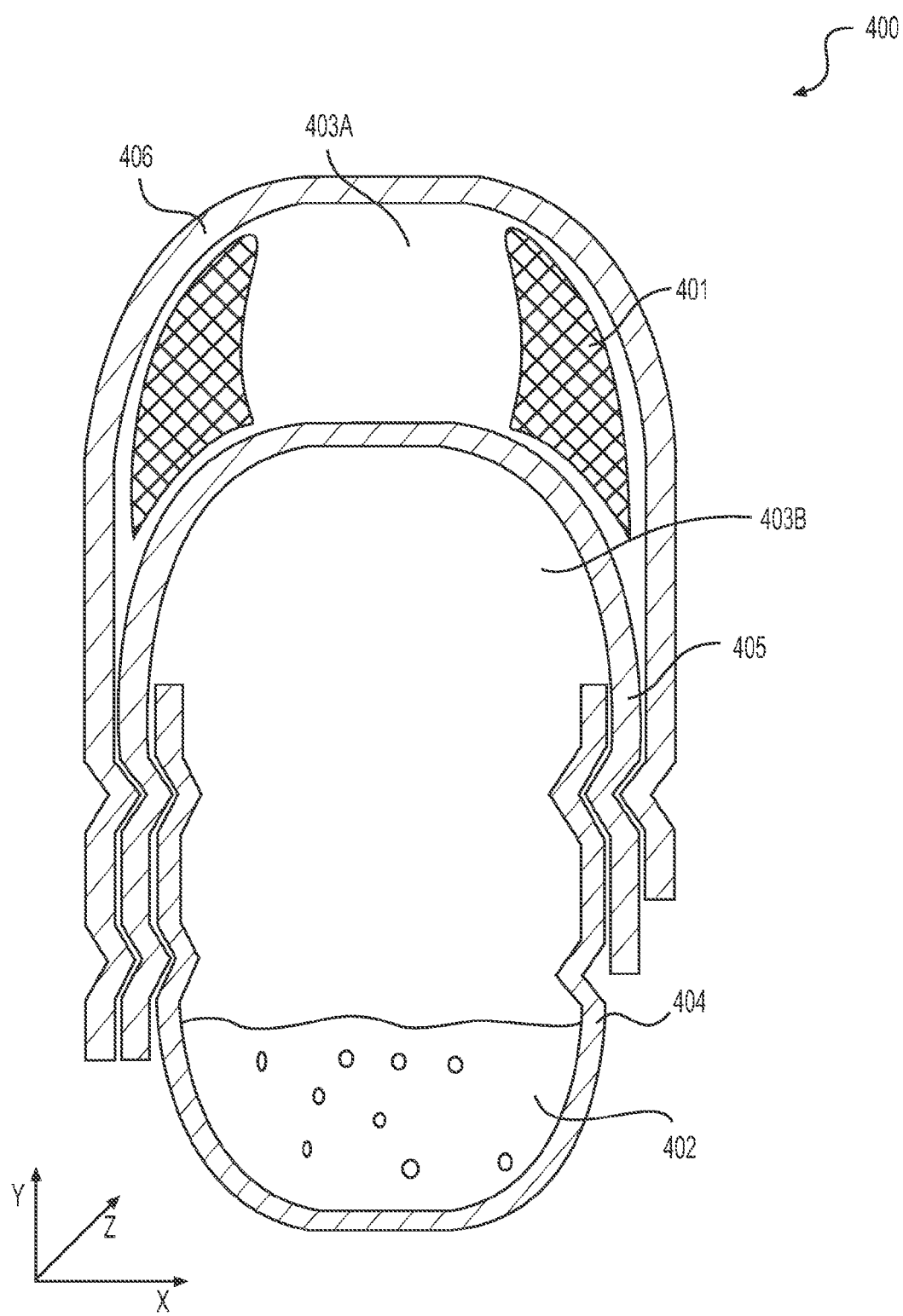
FIG. 4 is an illustration of a cross-sectional view of a dosage form article according to one aspect of the disclosure.

Referring to FIGS. 1, 3 and 4, the dosage form article 100, 300, 400 may comprise: at least one first body part 104, 304, 404 and at least one first cap part 105, 305, 405, wherein said first body and cap parts 104, 105, 304, 305, 404, 405 are telescopically engageable; and at least one second body 106, 306 or cap 406 part telescopically engageable with said at least one first body 104, 304, 404 or cap 105, 305, 405 parts or both, to provide one or more compartments 103a, 103b, 303a, 303b, 403a, 403b. This has the advantage of providing a very volume efficient multi-compartment dosage form, enabling for example size reduction for even better swallowability, which may be particularly desirable in pediatric or geriatric applications.

In an embodiment, at least a portion of the second body 106, 306 is engaged onto at least a portion of the inner or outer, preferably inner, surface of the first body or cap part, preferably first body part 104, 304, 404 so that the second body sits (or is arranged) within the first body part.

The dosage form article may comprise a plurality of second body or second cap parts, typically stored within one another (e.g. a first second body part storing therein a second second body part, said second second body part storing therein a third second body part etc.).

Preferably, each body and cap part may comprise a first cross-sectional area A1 and a second cross-sectional area A2, wherein the second cross-sectional area is less than or equal to the first cross-sectional area, and wherein the area ratio (i.e. second over first cross-sectional areas) of the at least one second body 106 or cap part is less than the area ratio of the first body part 104 and/or first cap part 105. This has the advantage of providing multiple compartments whilst further minimizing overall size of the dosage form and ensuring overall volume maximization. Moreover, it guarantees a secure fit allowing for simple location of the signaling means within its dedicated compartment in the dosage form article as well as ensuring ease of assembly and filling operations of each respective compartment.

The first and second cross-sectional areas may be substantially parallel to each other and distal from one another, preferably along a vertical plane parallel to a centerline of the dosage form article. The distance between the first and second area may be, for example, from 40% to 75%, preferably from 45% to 70%, more preferably from 50% to 70%, even more preferably from 60% to 70%, of the total length L of a cap 105 or body 106 part.

Typically, each body and/or cap parts are tapered such that the diameter of the closed end is smaller than the diameter of the open end of each body and/or cap parts. Preferably, the second body part or second cap part comprises more than one tapers arranged such that at least a first taper is proximal to the open end and at least a second taper is proximal to the closed end, the first taper may extend from a circumference of the body and/or cap parts towards a centerline Y. The first taper may be less than the second taper. The advantage of this configuration is to achieve cap and/or body parts having optimal shapes for being locked into each other for generating multi-compartment dosage form articles. It also ensures that the diameter of a lower portion of the cap/body part is substantially less than the diameter of an upper portion of the cap/body part in order to maximize available volume for the compartments whilst minimizing overall size of the dosage form. It also permits to securely lock the second body/cap parts within the first body/cap parts about respective positions proximal to the upper portion.

The second body or cap parts may have an upper portion 107 and a lower portion 108 adjacently located to respective first body and/or cap part upper and lower portions (when in assembled state), the ratio of the diameters of the upper and lower portions (i.e. diameter of upper portion over diameter of lower portion) of the second body or cap parts is greater than the respective upper and lower portion ratio of the first body and/or cap part.

The second cap 406 or body part 106, 306 may be solely telescopically engageable with the first body part 104, 304, 404 or first cap part 105, 305, 405, or both. This arrangement may bring advantages to ease of processing, particularly during the filling stages, as well as permitting effective sealing of multiple compartments when liquids are stored therein. Any known sealing method may be used, like banding or by sealing via a sealing liquid sealing and typically locking between adjacent surfaces of the body and cap via effects such as capillary action or pressure difference between the pressure within the dosage form and outside the dosage form (examples of such methods are provided for example on EP2049064B1, particularly in paragraphs 24 to 57, and US2013/0081358, particularly in paragraphs 41 to 58).

The second body part 106, 306 may be telescopically engageable with the first body part 104, 304, 404, or the second cap part 406 may be telescopically engageable with the first cap part 105, 305, 405.

Typically, a first compartment 103*a*, 303*a*, 403*a* may be formed, preferably only, between the first body part 104, 304, 404 and second body part 106, 306, or first cap part 105, 305, 405 and second cap part 406, for storing the signaling means 101, 301, 401 therein. A second compartment 103*b*, 303*b*, 403*b* may be formed, preferably only, between the second body part 106 and the first cap part 105, or first cap part 305, 405 and first body part 304, 404, for storing the drug 102, 202, 302, 402 therein.

The first body part 104 or second cap part 406 may be translucent such that the signaling means 101, 401 may be seen through said first body part 104 or second cap part 406. The second body part and/or the first cap part may be opaque.

Alternatively, the second body part 306 or second cap part 406 may be translucent such that the signaling means 301, 401 may be seen through said second body part 306 or second cap part 406. The first body and/or cap part may be opaque.

In an embodiment, the first body and cap parts 104, 304, 404, 105, 305, 405 and the second body 106, 306 or cap 406 parts are prevented from movement once engaged, preferably via, for example, a snap fit, such that no said parts may dislocate during handling of the dosage form. Such arrangement may introduce benefits such as reduced risk of damaging the signaling means during handling as well as accurate location of components within the dosage form, particularly in assembly and filling processes.

In an embodiment the dosage form articles herein are multi-piece capsules comprising a plurality of capsule shells. The capsule shells may each comprise locking features to mechanically lock with one or more other capsule shells. Said features may comprise a combination of protrusions and recesses of complementary shape such that when interposed lock the capsule shells together.

The dosage form articles herein may be made of, or consist of, an ingestible material comprising materials selected from the group consisting of gelatin, one or more polysaccharides, preferably pullulan; nonionic hydrogels, preferably cellulose such as hydroxy propyl methylcellulose (HPMC); and mixtures thereof. Most preferred materials being gelatin and/or HPMC. Dosage form articles herein may be non-injection molded, and/or preferably made via a dip molding process. The latter may ensure high production speeds and cost effectiveness. Other materials may also be used, as will be recognized by one skilled in the art, including cellulose ethers, such as starches (e.g. waxy maize starch, tapioca dextrin, and derivatives thereof), carrageenan, and polymers or copolymers of (meth)acrylic acids and derivatives thereof.

Typically, the cap and body parts may be substantially tubular in shape and each comprise a single opening. The cap and/or body parts described herein may be hard capsule shells.

Signaling Means

One or more signaling means are typically stored within dosage form articles described herein.

The signaling means 101, 201, 301,401 may be selected from the group consisting of an ingestible passive microelectronic system, preferably comprising, for example, a radio frequency emitter; ingestible indicia, preferably indicia that undergoes a visual transformation, such as color change, when exposed to predetermined physical changes, such as an increase in temperature over a predetermined amount or a change in color with time (or aging), or a barcode-like readable medium; and combinations thereof.

In one embodiment the signaling means is an ingestible passive micro-electronic system. The passive micro-electronic system may comprise an ingestible radio frequency emitter and a power source. The radio frequency emitter may comprise one or more antennas and preferably a processing unit.

The power source may use power conditioning to extract energy from electromagnetic fields and/or internal electrical sources generated by internal biological electrochemical interactions within the subject body. The power source may be arranged to use electrochemical reactions between internal gastric acid, oxidizing and reduction electrodes to activate the passive micro-electronic system and provide one or more signal bursts after reaching a predetermined position in the gastrointestinal tract (for example by reacting at a predetermined pH level).

The power source may, alternatively or in combination with the above described power conditioning, comprise a micro battery storing sufficient energy to power one or more signal bursts when activated.

The antenna may be designed to fold within a compartment of dosage form articles herein and arranged to deploy so as to expand its surface area versus the folded state but without exceeding the maximum surface area of the dosage form article. The advantage of this embodiment is the reduced risk of the antenna wrapping around part of the compartment storing the drug, when the antenna is deployed, which may otherwise delay its release from the desired predetermined position.

The dosage form article and/or the antenna may be arranged to deploy said antenna at a predetermined position in the gastrointestinal tract, the antenna may comprise one or more bio-compatible materials and may be free of protective coatings.

The processing unit may be in electrical communication with the antenna and arranged to provide a signal burst once activated by the power source, said signal burst then being transmitted by the antenna through the body of a subject to be captured and/or read by a receiver.

The radiofrequency emitter, typically including the antenna and processing unit, and the power source may be integrated into a single device to form the passive micro-electronic system. This has the advantage of easily locating all functional components within the dedicated compartment of the dosage form articles described herein, thus simplifying the assembly.

The ingestible passive micro-electronic system may further comprise one or more micro sensors preferably temperature and/or humidity sensors, arranged to record exposed temperature and humidity and send the information to the processing unit. In this embodiment the processing unit comprises a memory wherein maximum temperature and humidity parameters are stored, the processing unit further comprising a microprocessor for comparing the temperatures/humidity recorded by the sensor with the predetermined temperature/humidity parameter stored in the memory and arranged such that if the recorded measurement exceeds the predetermined parameter, a signal burst is generated. The signal burst may be delayed up to when a trigger is provided, for example by a subject scanning the dosage form article with a respective scanner and/or receiver. The advantage of this embodiment is that the subject may scan the dosage form article containing the signaling means therein and the signaling means will provide a signal to the receiver as to whether the parameters stored in the memory have been exceeded, i.e. the subject will know whether the dosage form has been exposed to e.g. excessively high temperatures which renders ingestion of the medicament unsafe.

It is understood herein that the sensor described herein above may take several forms and should not be limited to the above example. For example, the sensor may comprise a timer, the timer may be activated upon assembly of the dosage form. The microprocessor may be arranged to compare a preset time parameter stored in the memory with the reading of the timer, and once the reading of the timer exceeds the preset time parameter the processor is arranged to provide a signal burst. Like in the above example, the signal burst may be delayed up to when a trigger is provided, for example by a subject scanning the dosage form article with a respective scanner and/or receiver. In this case the advantage is that the subject may identify whether a medicament has expired by simply scanning the dosage form article containing the signaling means. This is particularly useful as one may identify whether safe to ingest a medicament directly by the dosage form without consulting the date on the box (e.g. in case misplaced, or label damaged/faded). The scanner/receiver may be arranged to provide a combinations of triggers to the user, for example visual and audio to instruct the subject whether a medicament has expired (or exposed to high temperatures etc.).

Alternatively or additionally, the signaling means may be ingestible indicia capable of changing color following a predetermined change in conditions or aging. The indicia may comprise florescent or phosphorescent agents. In a more preferred embodiment the signaling means comprises one or more indicating bodies, wherein the indicating bodies comprise one or more temperature sensitive or age sensitive materials, said materials typically capable of undergoing a chemical reaction when either exposed to a temperature above a predetermined maximum level or aging beyond a predetermined maximum time or both.

Temperature sensitive color changing materials are also known as thermochromic (or thermochromatic), and are typically selected from the group consisting of thermochormatic liquid crystals, leuco dyes, and mixtures thereof. Leuco dyes may be selected from one or more spirolactones, fluorans, spiropyrans, and mixtures thereof. Temperature sensitive color changing materials may undergo a permanent/irreversible color change when exposed to a temperature above a predetermined value.

In a preferred embodiment the indicating bodies may be in the form of microcapsules containing the thermochromatic materials therein. The microcapsules may be made of a material which is non-digestible and remains intact throughout the gastrointestinal tract until excreted as solid waste. The microcapsules may be, for example, from 200 µm to 3000 µm, preferably from 500 µm to 2000 µm, more preferable from 1000 µm to 2000 µm, in diameter.

Alternatively or additionally, the signaling means may be in the form of a barcode-like readable medium, preferably a barcode (e.g. one-dimensional or two-dimensional barcode). The barcode-like medium may store information such as the date of expiry of the drug stored in the dosage form article, the identity of the drug stored in the dosage form article etc. The subject may then be able to scan the barcode-like readable medium through the relevant portion of the dosage form article via the respective scanner and be provided with an indication of whether still safe to ingest (e.g. expiry date still not reached) and/or information as to the interval the scanned medicament should be taken. In an embodiment, the scanner may comprise a memory wherein information scanned is stored, and a programmable processor capable of comparing the information stored in the memory with the new information received when scanning a dosage form article and provide a signal in case the detected drug is incompatible with a previously taken drug, or whether the time interval from the previously taken drug does not meet predetermined criteria. This is particularly advantageous for subjects who are taking multiple medicaments (for one or more treatments) and is important to time the administration, as well as to aid the subject to stay within the administration regimen provided by the prescriber. In an embodiment, only the prescriber may input the required parameters in the scanner to program the processor, the scanner having an access key preventing the subject to modify the program of the programmable processor.

Drug/Medicament

Dosage form articles described herein may comprise one or more drugs. Drugs suitable for use in the dosage forms described herein may take any form and be for any treatment of a human or animal subject. This includes not only pharmaceutical compounds but also dietary supplements such as vitamins, minerals and the like.

The drug may be in a state selected from solid or liquid, at room temperature and atmospheric pressure, and comprises one or more active compounds. The physical state of said drug is typically wholly dependent on the needs for a given application. When the drug is in solid state the drug may be powder-like or caplet-like (i.e. tablet-like). In an embodiment, the drug is in the form of a caplet or tablet typically having a first and second end. The caplet or tablet may be further coated, alternatively or additionally, at least one, preferably both, first and second ends of the caplet or tablet may be coated with capsule shells. The capsule shells may be gelatin comprising or hydroxypropyl methylcellulose (HPMC) comprising shells. By "capsule shells" it is herein intended at least portions of body or cap parts of hard capsule shells out to size such to fit and insert over the outer surface of the caplet or tablet to provide a tight fit when joined. The capsule shells may be further treated following insertion over the caplet or tablet such to firmly adhere thereto, preferably by shrinking.

Suitable compounds for delivery according to the disclosure include, but are not limited to, powder, liquid, and/or pellet forms of the following:

pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovir-mononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydro genmaleate, bezafibrate, isosorbide dinitrate, gallopamil, xantinolnicofinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclo-pramide, acemetacin, ranitidine, biperiden, metamizol, doxepin, dipotassiumchloraze-pat, tetrazepam, estramustinephosphate, terbutaline, captopril, maprotiline, prazosin, atenolol, glibenclamid, cefaclor, etilefrin, cimetidine, theophylline, hydromorphone, ibu-profen, primidone, clobazam, oxaceprol, medroxyprogesterone, flecainide, Mg-pyhdoxal-5-phosphateglutaminate, hymechromone, etofyllineclofibrate, vincamine, cin-narizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloguine, probucol, quinidine, carbamazepine, Mg-1-aspartate, penbutolol, piretanide, amitriptyline, caproteron, sodium valproinate, mebeverine, bisacodyl, 5-amino-salicylic acid, dihydralazine, magaldrate, phenprocou-mon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cin-narizine, clonazepam, codeine, dexamethasone, dicumarol, digoxin, drotaverine, grami-cidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbi-tal, phenylbutazone, phenytoin, prednisone, reserpine, spironolactine, streptomycin, sul-famethizole, sulfamethazine, sulfamethoxazole, sulfamethondiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, anti-depressants (including tricyclic antidepressants, monoamine oxidase inhibitors, lithium salts, selective serotonin reuptake inhibitors), anti-emetics, anticonvulsants, an-tiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosponate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di-ethylstilbestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present disclosure includes homeopathic ingredients that may be added to the HPRS; and mixtures in any combination of the foregoing.

It is also contemplated that mixtures of compatible ingredients can be included in one compartment and other ingredients which are not compatible with the contents of one compartment or other ingredients which are desirably placed in another compartment can also be used as part of the present disclosure. For example, a first compound may be included in one compartment in a powdered dosage form while a second compound may be included in a second compartment in a liquid dosage form. The ability to administer different dosage forms in a single dosage unit avoids not only any incompatibilities between the compounds and/or their dosage forms, but also the expense often incurred in reformulating one or the other compound into a compatible dosage form.

Methods

Dosage form articles as described herein may be used in a number of methods and applications, the below passages will describe some of the methods in which dosage form articles as described may be particularly useful.

A method of measuring compliance with a medical regimen may comprise the steps of: administering to a subject a dosage form; providing a receiver for detecting a signal produced by the signaling means preferably when the dosage form reaches a predetermined position in the gastrointestinal tract of the subject; and optionally recording administration parameters via a recording device which may be in electrical communication with said receiver, said administration parameters preferably selected from the group consisting of date, time, and combinations thereof. Such method has the advantage of ensuring complete traceability and adherence to a medical regimen. By digitally logging information of when a given dosage form or array of dosage forms are ingested, such information may be easily and reliably extracted for a number of further studies as well as ensuring compliance with a medical regimen.

Further or as an alternative to the above method, a method for determining whether it is safe to ingest a medicament may comprise the steps of: providing a dosage form article; comparing a signal received by the signaling means to a predetermined scale to instruct a subject whether he should or should not ingest said dosage form. The predetermined scale may be in the form of a written scale provided with the medicament and/or stored on a website and/or cloud computing, the latter such that it may be accessed by the subject or user via the use of any personal computer or even directly by a scanner and/or receiver (as described above) that the subject may use to capture the signal from the signaling means (the latter especially when a passive micro-electronic system is used as signaling means).

The signal may be a visual signal, preferably a color signal, and the signaling means may be in the form of indicia capable of changing color when the medicament is no longer safe to be ingested, and preferably the scale indicates what the visual signal stands for. In this case, the subject or user may manually compare the visual signal received by the signaling means to the predetermined scale and assesses its meaning. For example, if the visual signal received and/or read by the subject is identical or equal to that represented in the predetermined scale as an indication that the dosage form article has been exposed to a temperature above a critical predetermined value, then the subject or user knows that it is not safe to ingest the medicament. It is apparent that the comparison may be done also electronically by scanning the signaling means with a scanning and/or receiving device and allowing it to compare the input signal with the predetermined scale via corresponding processor. It is also apparent that when the signaling means is a passive micro-electronic system, the comparison is achieved electronically via e.g. a processor (as described in the signaling means section above), the subject or user being thus directly informed of the final answer as to safe or not safe to ingest.

Figure 5A:
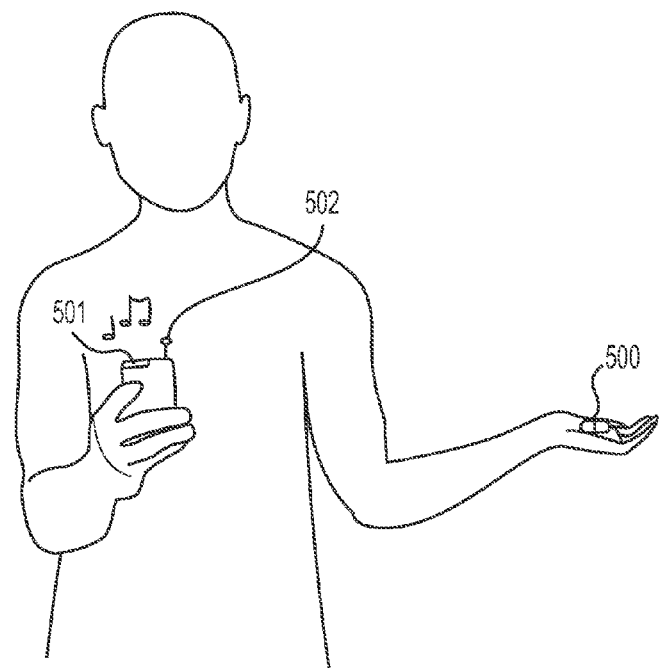
FIG. 5A is an illustration of the operation of a method providing a warning, according to an aspect of the disclosure.
Figure 5B:
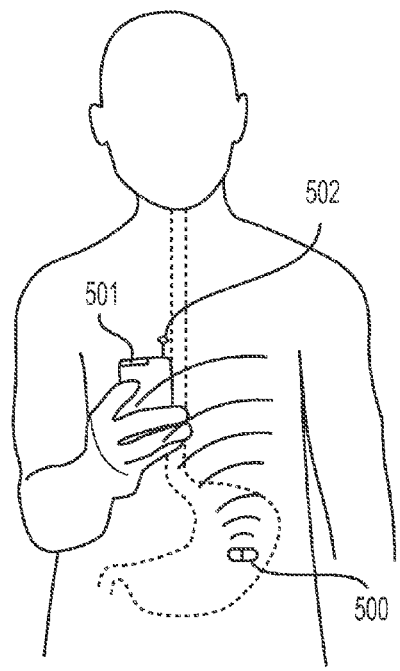
FIG. 5B is an illustration of the operation of the method to stop providing a warning, according to an aspect of the disclosure.

Further or as an alternative to the above method, a method for the automatic prompting of a subject to take a medicament. FIGS. 5A and 5B showing an exemplary illustration of the method, the method comprising the steps of: providing a portable communication device 501 arranged to provide a warning (FIG. 5A), preferably selected from visual, sound, and combinations thereof, to a subject when it is time to ingesta medicament; providing a dosage form 100, 200, 300, 400, 500 as described herein; providing a receiver 502 capable of detecting a signal generated by the signaling means, the receiver being arranged to provide a further signal to a processing device, the processing device capable of recording said further signal and to instruct the communication device 501 to stop providing said warning (FIG. 5B); and allowing said receiver 502 to detect said signaling means; wherein said warning is de-activated only when the subject places said receiver 502 proximal to said dosage form 100, 200, 300, 400, 500, and the signaling means stored therein is detected.

The communication device may comprise a re-programmable timer arranged such that once a predetermined time is reached, the warning is triggered. The re-programmable timer may be re-set only after the signal from the signaling means is detected. At this point a new count-down may begin before a second warning is provided to instruct the subject to take the next dose. The process may be repeated a plurality of times.

Typically the signaling means is detected by the receiver 502 only after the dosage form article 100, 200, 300, 400, 500 is ingested. In these embodiments the signaling means may be arranged to trigger a signal only when the dosage form article is at a predetermined position in the gastrointestinal tract, such that the receiver only detects the signal at this point and only at this point the portable communication device is instructed to stop the warning. This may be achieved by any of the respective arrangements described above, such as via use of a power source generating energy to power a signal burst only when reacting with in-body acids. This has the advantage that the subject is prompted when a given medicament must be taken, the prompting ending only when the signaling means is scanned, detected and/or drug ingested, thus ensuring that the subject strictly keeps to a given medical regimen. This may be particularly important for medications wherein strict compliance (e.g. frequency and time) must be controlled and ensured.

The disclosure herein encompasses a method of assembly, of dosage form articles described herein, typically comprising the steps of: providing a first body part; inserting a signaling means within the first body part; providing a second body part; filling said second body part with a drug; optionally closing said second body part by locking a second cap part thereon; inserting said second body part within said first body part such that the signaling means is further located into a firm position between said first and second body parts; and closing said first body part by locking a first cap part thereon.

In a preferred embodiment the method of assembly comprises the sequential steps of: providing a first body part; inserting a signaling means within the first body part; providing a second body part; inserting said second body part within said first body part such that the signaling means is further located into a firm position between said first and second body parts and typically such that a volume in the first body part is closed off by the second body part to form a signaling means compartment; optionally locking said second body part to said first body part typically via a snap fit; filling said second body part with a drug; and closing said second body part by locking a first cap part onto said second body part, first body part or both, typically via a snap fit. It is understood by a person skilled in the art that the same method of assembly may be carried out also when a plurality of second body parts are used, e.g. in the latter case of a further second body part the steps are repeated but with the further second body part replacing the second body part and the second body part replacing the first body part (for example: providing a further second body part; inserting said further second body part within said second body part; optionally locking said further second body part to said second body part typically via a snap fit; filling said further second body part with a drug; and closing said further second body part by locking a first cap part onto said further second body part, first body part or both, typically via a snap fit.). This may be repeated for any number of further second body parts depending on the number of compartments desired. It is further understood that the above steps may be performed at any time and by the same or different entities provided the overall steps are performed in sequence.

The second body part may be locked to the first body part, typically after a filling step (e.g. insertion of a signaling means in the first body part), such that a second assembly or filling operation may be carried out to fill the second body part followed by closing the dosage form, typically by fully locking a first cap part with the first body part, or second body part or both.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" (i.e. every value in a practical range close to 40 mm).

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

The invention claimed is:

1. A dosage form article suitable for oral administration, comprising more than one compartment each formed by a plurality of distinct segments of the dosage form article, said dosage form article comprising a signaling means and a drug, wherein each compartment comprises a definite volume for storing a drug, or signaling means therein, formed and delimited by the plurality of distinct segments when connected to each other, wherein said signaling means and said drug are each stored in different compartments physically separated from one another, wherein both the drug and the signaling means are wholly incorporated within the dosage form article, the respective compartments being arranged to fully enclose the drug and signaling means only when at least two of the plurality of distinct segments are connected, and wherein each said distinct segment consists of a cap part or a body part and said cap and/or body parts are hard capsule shells.

2. A dosage form article according to claim 1, wherein at least a portion of the dosage form article is translucent such that the signaling means is visible through said dosage form.

3. A dosage form article according to claim 1, wherein the compartment storing the signaling means and the compartment storing the drug have different dissolution properties, wherein the compartment storing said signaling means is arranged to disintegrate faster than the compartment storing the drug.

4. A dosage form article according to claim 1, wherein the dosage form article comprises:
at least one first body part and at least one first cap part, wherein said first body and cap parts are telescopically engageable to provide a first compartment; and
at least one second body part and at least one second cap part, wherein said second body and cap parts are telescopically engageable to provide a second compartment;
wherein said second compartment is stored within said first compartment, the signaling means being stored within the first or second compartment and the drug being stored within the first or second compartment, and wherein said signaling means and said drug are stored in different compartments.

5. A dosage form article according to claim 4, wherein the signaling means is stored within the first compartment and the drug is stored within the second compartment, wherein the first body and/or cap parts are translucent such that the signaling means may be seen through the first compartment.

6. A dosage form article according to claim 1, wherein the dosage form article comprises:
at least one first body part and at least one first cap part, wherein said first body and cap parts are telescopically engageable; and
at least one second body or cap part telescopically engageable with said at least one first body or cap parts or both, to provide one or more compartments.

7. A dosage form article according to claim 6, wherein the second cap or body part is solely telescopically engageable with the first body part or first cap part.

8. A dosage form article according to claim 6, wherein the second body part is telescopically engageable with the first body part, or the second cap part is telescopically engageable with the first cap part.

9. A dosage form article according to claim 6, wherein a first compartment is formed between the first body part and second body part, or first cap part and second cap part, for storing the signaling means therein, and wherein a second compartment is formed between the second body part and the first cap part, or first cap part and first body part, for storing the drug therein.

10. A dosage form article according to claim 9, wherein the first body part or second cap part is translucent such that the signaling means can be seen through said first body part or second cap part.

11. A dosage form article according to claim 9, wherein the second body part is translucent such that the signaling means can be seen through said second body part or second cap part.

12. A dosage form article according to claim 1, wherein the signaling means is selected from the group consisting of an ingestible passive micro-electronic system; ingestible indicia; and combinations thereof.

13. A method for the automatic prompting of a subject to take a medicament, the method comprising the steps of;
   providing a portable communication device arranged to provide a warning selected from visual, sound, and combinations thereof, to a subject when it is time to ingest a medicament;
   providing a dosage form article according to claim 1;
   providing a receiver capable of detecting a signal generated by the signaling means, the receiver being arranged to provide a further signal to a processing device, the processing device capable of recording said further signal and to instruct the portable communication device to stop providing said warning; and
   allowing said receiver to detect said signaling means;
   wherein said warning is de-activated only when the subject places said receiver proximal to said dosage form, and the signaling means stored therein is detected.

14. A method for determining whether it is safe to ingest a medicament comprising the steps of:
   providing a dosage form according to claim 1;
   comparing a signal received by the signaling means to a predetermined scale to instruct a subject whether he should or should not ingest said dosage form.

15. The method of claim 13 wherein the warning is de-activated only when the signaling means is detected by the receiver, only after the dosage form article is ingested.

16. A dosage form article comprising:
   an article suitable for oral administration, the article having
     a plurality of compartments each formed by a plurality of distinct segments of the article;
     a signal emitter; and
   wherein the compartments define a volume for storing the drug or signal emitter therein, each volume formed by the plurality of the segments when connected to one another and
   a drug, wherein the signal emitter and the drug are each stored in different compartments physically separated from one another, and wherein both the drug and the signaling emitter are wholly incorporated within the dosage form article, the respective compartments being arranged to fully enclose the drug and signaling emitter only when at least two of the plurality of distinct segments are connected, wherein the signal emitter is insertable into the compartment prior to connection of the at least two of the plurality of distinct segments, and wherein each distinct segment includes of a cap part or a body part and the cap and/or body parts are hard capsule shells.

17. A dosage form article suitable for oral administration, the dosage form article comprising:
   first, second and third distinct segments of the dosage form article;
   a plurality of compartments, each formed by at least two of the first, second and third distinct segments of the dosage form article;
   a signaling means stored in a signaling means compartment in the first segment; and
   a drug compartment configured to maintain a drug in the second segment;
   wherein the signaling means compartment and the drug compartment are wholly incorporated within the dosage form article, the respective compartments being arranged to fully enclose the drug and signaling means only when the first, second and third distinct segments are connected, wherein each of the first, the second, and the third segments include a cap part or a body part and the cap and/or body parts are hard capsule shells.

* * * * *

UNITED STATES PATENT AND TRADEMARK OFFICE
CERTIFICATE OF CORRECTION

PATENT NO. : 9,980,905 B2  
APPLICATION NO. : 15/032601  
DATED : May 29, 2018  
INVENTOR(S) : Buydts et al.

Page 1 of 1

It is certified that error appears in the above-identified patent and that said Letters Patent is hereby corrected as shown below:

In the Specification

Column 11, Line 15, "out to size" should read --cut to size--.

Column 14, Lines 4-5, "medicament. FIGS 5A" should read --medicament, FIGS 5A--.

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*